United States Patent [19]
Howell et al.

[11] Patent Number: 6,159,470
[45] Date of Patent: Dec. 12, 2000

[54] VACCINATION AND METHODS AGAINST DISEASES RESULTING FROM PATHOGENIC RESPONSES BY SPECIFIC T CELL POPULATIONS

[75] Inventors: Mark D. Howell, San Diego; Steven W. Brostoff, Carlsbad; Dennis J. Carlo, Rancho Santa Fe, all of Calif.

[73] Assignee: The Immune Response Corporation, Carlsbad, Calif.

[21] Appl. No.: 08/464,506

[22] Filed: Jun. 5, 1995

Related U.S. Application Data

[62] Division of application No. 08/376,049, Jan. 20, 1995, Pat. No. 5,837,246, which is a continuation of application No. 08/010,483, Jan. 28, 1993, abandoned, which is a continuation of application No. 07/530,229, May 30, 1990, abandoned, which is a continuation-in-part of application No. 07/382,085, Jul. 18, 1989, abandoned, and a continuation-in-part of application No. 07/382,086, Jul. 18, 1989, abandoned, and a continuation-in-part of application No. 07/326,314, Mar. 21, 1989, abandoned.

[51] Int. Cl.[7] .................................................. A61K 39/395
[52] U.S. Cl. ...................... 424/173.1; 424/144.1; 424/154.1; 424/183.1; 424/578; 530/387.1; 530/391.3; 530/391.7; 530/389.6
[58] Field of Search .............................. 424/144.1, 154.1, 424/183.1, 578, 173.1; 530/387.1, 391.3, 391.7, 389.6

[56] References Cited

U.S. PATENT DOCUMENTS

| | | |
|---|---|---|
| 4,886,743 | 12/1989 | Hood et al. . |
| 5,189,147 | 2/1993 | Saito . |
| 5,223,426 | 6/1993 | Skibbens . |

FOREIGN PATENT DOCUMENTS

| | | |
|---|---|---|
| WO-A-86/06413 | 11/1986 | WIPO . |
| WO 91/01133 | 2/1991 | WIPO . |

OTHER PUBLICATIONS

Ben–Nun et al., Vaccination against autoimmune encephalomyelitis with T–lymphocyte line cells reactive against myelin basic protein. *Nature* 292:60–61 (1981).

Acha–Orbea et al., Limited heterogeneity of T cell receptors from lymphocytes mediating autoimmune encephalomyelitis allows specific immune intervention. *Cell* 54:263–273 (1988).

Urban et al., Restricted use of T cell receptor V genes in murine autoimmune encephalomyelitis raises possibilities for antibody therapy. *Cell* 54:577–592 (1988).

Owhashi and Heber–Katz, Protection from experimental allergic encephalomyelitis conferred by a monoclonal antibody directed against a shared idiotype on rat T cell receptors specific for myelin basic protein. *J. Exp. Med.* 168:2153–2164 (1988).

(List continued on next page.)

*Primary Examiner*—Christina Y. Chan
*Assistant Examiner*—Martha Lubet
*Attorney, Agent, or Firm*—Campbell & Flores LLP

[57] ABSTRACT

The present invention provides vaccines and a means of vaccinating a mammal so as to prevent or control specific T cell mediated pathologies or to treat the unregulated replication of T cells. The vaccine is composed of a T cell receptor (TCR) or a fragment thereof corresponding to a TCR present on the surface of T cells mediating the pathology. The vaccine fragment can be a peptide corresponding to sequences of TCRs characteristic of the T cells mediating said pathology. Means of determining appropriate amino acid sequences for such vaccines are also provided. The vaccine is administered to the mammal in a manner that induces an immune response directed against the TCR of T cells mediating the pathology. This immune response down regulates or deletes the pathogenic T cells, thus ablating the disease pathogenesis. The invention additionally provides a specific β-chain variable region of the T cell receptor, designated Vβ17, which is central to the pathogenesis of rheumatoid arthritis (RA). Also provided are means to detect, prevent and treat RA.

2 Claims, 2 Drawing Sheets

OTHER PUBLICATIONS

Burns et al., Both rat and mouse T cell receptors specific for the encephalitogenic determinant of myelin basic protein use similar V α and V β chain genes even though the major histocompatibility complex of encephalitogenic determinants being recognized are different. *J. Exp. Med.* 169:27–39 (1989).

Chluba et al., T cell receptor β chain usage in myelin basic protein–specific rat T lymphocytes. *Eur. J. Immunol.* 19:279–284 (1989).

Wucherpfennig et al., Shared human T cell receptor Vβ usage to immunodominant regions of myelin basic protein. *Science* 248:1016–1019 (1990).

Kimura et al., Sequences and repertoire of the human T cell receptor α and β chain variable region genes in thymocytes. *Eur. J. Immunol.* 17:375–383 (1987).

Sedgwick, J., Long–term depletion of $CD8^+$ T cells in vivo in the rat: no observed role for $CD8^+$ (cytotoxic/ suppressor) cells in the immunoregulation of experimental allergic encephalomyelitis. *Eur. J. Immunol.* 18:495–502 (1988).

Zamvil et al., Predominant expression of a T cell receptor $V_\beta$ gene subfamily in autoimmune encephalomyelitis, *J. Exp. Med.* 167:1586–1596 (1988).

Lider et al., Anti–idiotypic network induced by T cell vaccination against experimental autoimmune encephalomyelitis. *Science* 239:181–183 (1988).

Sun et al., Suppression of experimentally induced autoimmune encephalomyelitis by cytolytic T–T cell interactions. *Nature* 332:843–845 (1988).

Offner et al., Lymphocyte vaccination against experimental autoimmune encephalomyelitis: evaluation of vaccination protocols. *J. Neuroimmunol.* 21:13–22 (1989).

Choi et al., Interaction of *Staphylococcus aureus* toxin "superantigens" with human T cells. *Proc. Natl. Acad. Sci. USA* 86:8941–8945 (1989).

White et al., The Vβ–specific superantigen staphylcoccal enterotoxin B: stimulation of mature T cells and clonal deletion in neonatal mice. *Cell* 56:27–35 (1989).

Pullen et al., Identification of the region of T cell receptor β chain that interacts with the self–superantigen M1s–$1^a$. *Cell* 61:1365–1374 (1990).

Janeway, C., Self superantigens? *Cell* 63:659–661 (1990).

Marrack and Kappler, The staphylococcal enterotoxins and their relatives. *Science* 248:705–711 (1990).

Yanagi et al., A human T cell–specific cDNA clone encodes a protein having extensive homology to immunoglobulin chains. *Nature* 308:145–149 (1984).

Biddison et al., The germline repertoire of T–cell receptor beta–chain genes in patients with multiple sclerosis. *Res. Immunol.* 140:212–215 (1989).

Ross et al., Antibodies to synthetic peptides corresponding to variable–region first–framework segments of T cell receptors. *Immunol. Res.* 8:81–87 (1989).

Schluter et al., Antibodies to synthetic joining segment peptide of the T–cell receptor β–chain: serological cross–reaction between products of T–cell receptor genes, antigen binding T–cell receptors and immunoglobulns. *Chem. Abstracts* 105(1):464, abstract No. 47679 (1986).

Howell et al., Vaccination against experimental allergic encephalomyelitis with T cell receptor peptides. *Science* 246(4930):668–670 (1989).

Vandenbark et al., Immunization with a synthetic T–cell receptor V–region peptide protects against experimental autoimmune encephalomyelitis. *Letters to Nature* 341:541–544 (1989).

Patten et al., Structure, expression and divergence of T–cell receptor β–chain variable regions, *Nature* 312:40–46 (1984).

Acha–Orbea Ann. Rev. Immunol. 7:371–405, 1989.

Padula et al J. Immunol. 146: 879, 1991.

Wofsy et al J. of Exp Med 161: 378, 1985.

Ranges et al. J. Exp. Med 162: 1105, 1985.

Wooley et al. J. of Immunol. 134: 2366, 1985.

Hafler et al 1996 Immunol Today 17:152.

Wraith et al 1989 Cell 57:709.

Kappler et al. 1987 Cell 49:263.

Janson et al. 1989 Cancer Immunol Immunother. 28:225.

VACCINATION AND METHODS AGAINST DISEASES RESULTING FROM PATHOGENIC RESPONSES BY SPECIFIC T CELL POPULATIONS

This application is a divisional of U.S. application Ser. No. 08/376,049, filed Jan. 20, 1995, now U.S. Pat. No. 5,837,246 which is a continuation of application Ser. No. 08/010,483 filed Jan. 28, 1993 now abandoned; which is a continuation of U.S. Ser. No. 07/530,299 filed May 30, 1990 now abandoned; which is a continuation-in-part of U.S. Ser. No. 07/382,085 filed Jul. 18, 1989, now abandoned and of U.S. Ser. No. 07/382,086 filed Jul. 18, 1989 now abandoned; which are continuations-in-part of U.S. Ser. No. 07/326,314 filed Mar. 21, 1989, now abandoned the entire contents of which are incorporated by reference herein.

BACKGROUND OF THE INVENTION

This invention relates to the immune system and, more specifically, to methods of modifying pathological immune responses.

Higher organisms are characterized by an immune system which protects them against invasion by potentially deleterious substances or microorganisms. When a substance, termed an antigen, enters the body, and is recognized as foreign, the immune system mounts both an antibody-mediated response and a cell-mediated response. Cells of the immune system termed B lymphocytes, or B cells, produce antibodies which specifically recognize and bind to the foreign substance. Other lymphocytes termed T lymphocytes, or T cells, both effect and regulate the cell-mediated response resulting eventually in the elimination of the antigen.

A variety of T cells are involved in the cell-mediated response. Some induce particular B cell clones to proliferate and produce antibodies specific for the antigen. Others recognize and destroy cells presenting foreign antigens on their surfaces. Certain T cells regulate the response by either stimulating or suppressing other cells.

While the normal immune system is closely regulated, aberrations in immune response are not uncommon. In some instances, the immune system functions inappropriately and reacts to a component of the host as if it were, in fact, foreign. Such a response results in an autoimmune disease, in which the host's immune system attacks the host's own tissue. T cells, as the primary regulators of the immune system, directly or indirectly effect such autoimmune pathologies.

Numerous diseases are believed to result from autoimmune mechanisms. Prominent among these are rheumatoid arthritis, systemic lupus erythematosus, multiple sclerosis, Type I diabetes, myasthenia gravis and pemphigus vulgaris. Autoimmune diseases affect millions of individuals worldwide and the cost of these diseases, in terms of actual treatment expenditures and lost productivity, is measured in billions of dollars annually. At present, there are no known effective treatments for such autoimmune pathologies. Usually, only the symptoms can be treated, while the disease continues to progress, often resulting in severe debilitation or death.

In other instances, lymphocytes replicate inappropriately and without control. Such replication results in a cancerous condition known as a lymphoma. Where the unregulated lymphocytes are of the T cell type, the tumors are termed T cell lymphomas. As with other malignancies, T cell lymphomas are difficult to treat effectively.

Thus there exists a long-felt need for an effective means of curing or ameliorating T cell mediated pathologies. Such a treatment should ideally control the inappropriate T cell response, rather than merely reducing the symptoms. The present invention satisfies this need and provides related advantages as well.

SUMMARY OF THE INVENTION

The present invention provides vaccines and a means of vaccinating a mammal so as to prevent or control specific T cell mediated pathologies or to treat the unregulated clonal replication of T cells. The vaccine is composed of a T cell receptor (TCR) or a fragment thereof corresponding to a TCR present on the surface of T cells mediating the pathology. The vaccine fragment can be a peptide corresponding to sequences of TCRs characteristic of the T cells mediating said pathology.

Means of determining appropriate amino acid sequences for such vaccines are also provided. The vaccine is administered to the mammal in a manner that induces an immune response directed against the TCR of T cells mediating the pathology. This immune response down regulates or deletes the pathogenic T cells, thus ablating the disease pathogenesis.

The invention additionally provides a specific β-chain variable region of the T cell receptor, designated Vβ17, which is central to the pathogenesis of rheumatoid arthritis (RA). Also provided are means to detect, prevent and treat RA.

The invention also provides a specific region of a T cell receptor useful for the treatment of multiple sclerosis (MS). Also provided are means to detect, prevent and treat MS.

DETAILED DESCRIPTION OF THE INVENTION

Figure 1A:
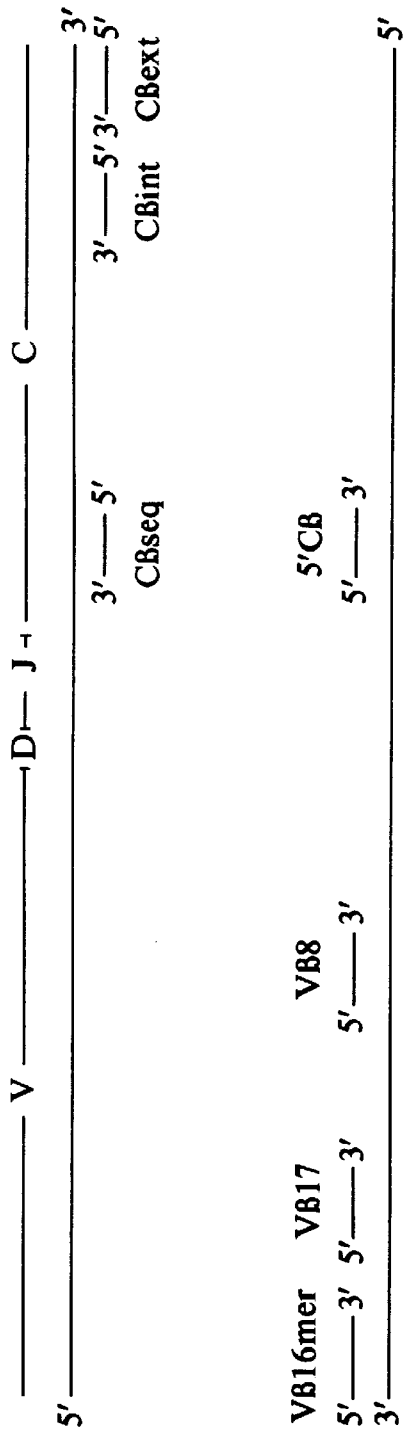
FIG. 1A) shows the location of primers used in polymerase chain reaction amplification of T cell receptor β-chain genes, B) shows primer sequences used in polymerase chain reaction.

The invention relates to vaccines and their use for preventing or ameliorating T cell-mediated pathologies, such as autoimmune diseases and T cell lymphomas. Vaccination provides a specific and sustained treatment which avoids problems associated with other potential avenues of therapy.

As used herein, the term "T cell-mediated pathology" refers to any condition in which an inappropriate T cell response is a component of the pathology. The term is intended to include both diseases directly mediated by T cells and those, such as myasthenia gravis, which are characterized primarily by damage resulting from antibody binding, and also diseases in which an inappropriate T cell response contributes to the production of those antibodies. The term is intented to encompass both T cell mediated autoimmune diseases and unregulated clonal T cell replication.

As used herein, "substantially the amino acid sequence", or "substantially the sequence" when referring to an amino acid sequence, means the described sequence or other sequences having any additions, deletions or substitutions which do not substantially effect the ability of the sequence to elicit an immune response against the desired T cell receptor sequence. Such sequences commonly have many other sequences adjacent to the described sequence. A portion of the described immunizing sequence can be used so long as it is sufficiently characteristic of the desired T cell receptor as to cause an effective immune response against desired T cell receptors but not against undesired T cell receptors. Such variations in the sequence can easily be made, e.g. by synthesizing an alternative sequence, and tested, e.g. by immunizing a mammal, to determine its effectiveness.

As used herein, the term "fragment" is intended to cover such fragments in conjunction with or combined with additional sequences or moieties, as for example where the peptide is coupled to other amino acid sequences or to a carrier. The terms "fragment" and "peptide" can, therefore, be used interchangeably since a peptide will be the most common fragment of the T cell receptor. Each fragment of the invention can have an altered sequence, as described above for the term "substantially the sequence."

Reference herein to a "fragment or portion of the T cell receptor" does not mean that the composition must be derived from intact T cell receptors. Such "fragments or portions" can be produced by various means well-known to those skilled in the art, such as for example manual or automatic peptide synthesis or methods of cloning.

As used herein when referring to the relationship between peptide fragments of the invention and sequences of TCRs, "corresponding to" means that the peptide fragment has an amino acid sequence which is sufficiently homologous to the TCR sequence to stimulate an effective regulatory response in the individual. The sequence need not be identical to the TCR sequence, however, as shown in Examples II and III.

By "immunogenically effective" is meant an amount of the T cell receptor or fragment thereof which, is effective to elicit an immune response to prevent or treat a T cell mediated pathology or an unregulated T cell clonal replication in the individual. Obviously, such amounts will vary between species and individuals depending on many factors. For example, higher doses will generally be required for an effective immune response in a human compared with a mouse.

As used herein, "Vβ17" refers to a specific β-chain variable region of a T cell receptor (TCR). Vβ17 has the amino acid sequence MSNQVLCCVVLCFLGANTVDG-GITQSPKYLFRKEGON VTLSCEQNLNHDAMYW-YRQDPGQGLRLIYYSQIVNDFQKGDIA-EGYSVSREKKESFP LTVTSAQKNPTAFYLCASS. The hypervariable and junctional regions are most useful for vaccines. One hypervariable region of Vβ17 especially useful is the CDR2 region which has the amino acid sequence SQIVNDFQK. Modifications in this sequence which do not affect the ability of the receptor to act as an immunogen to stimulate the desired immune response are also included in the definition. The variable region can be joined with any D and J segment of the TCR. Further, immunogenicly representative fragments of Vβ17 are also included in the definition of "Vβ17."

As used herein, "binding partner" means a compound which is reactive with a TCR. Generally, this compound will be a Major Histocompatibility Antigen (MHC) but can be any compound so long as when the TCR is bound in the normal course, T cell activation or proliferation occurs.

As used herein, "ligand" means any molecule that reacts to form a complex with another molecule.

As used herein, "selectively binds" means that a molecule binds to one type of molecule but not substantially to other types of molecules. In relation to Vβ17 "selective binding" indicates binding to Vβ17 containing TCRs but not substantially to other TCRs which lack Vβ17.

The immune system is the primary biological defense of the host (self) against potentially pernicious agents (non-self). These pernicious agents may be pathogens, such as bacteria or viruses, as well as modified self cells, including virus-infected cells, tumor cells or other abnormal cells of the host. Collectively, these targets of the immune system are referred to as antigens. The recognition of antigen by the immune system rapidly mobilizes immune mechanisms to destroy that antigen, thus preserving the sanctity of the host environment.

The principal manifestations of an antigen-specific immune response are humoral immunity (antibody mediated) and cellular immunity (cell mediated). Each of these immunological mechanisms are initiated through the activation of helper (CD4+) T Cells. These CD4+ T cells in turn stimulate B cells, primed for antibody synthesis by antigen binding, to proliferate and secrete antibody. This secreted antibody binds to the antigen and facilitates its destruction by other immune mechanisms. Similarly, CD4+ T cells provide stimulatory signals to cytotoxic (CD8+) T cells which recognize and destroy cellular targets (for example, virus infected cells of the host). Thus, the activation of CD4+ T cells is the proximal event in the stimulation of an immune response. Therefore, elaboration of the mechanisms underlying antigen specific activation of CD4+ T cells is crucial in any attempt to selectively modify immunological function.

T cells owe their antigen specificity to the T cell receptor (TCR) which is expressed on the cell surface. The TCR is a heterodimeric glycoprotein, composed of two polypeptide chains, each with a molecular weight of approximately 45 kD. Two forms of the TCR have been identified. One is composed of an alpha chain and a beta chain, while the second consists of a gamma chain and a delta chain. Each of these four TCR polypeptide chains is encoded by a distinct genetic locus containing multiple discontinuous gene segments. These include variable (V) region gene segments, junction (J) region gene segments and constant (C) region gene segments. Beta and delta chains contain an additional element termed the diversity (D) gene segment. (Since D segments and elements are found in only some of the TCR genetic loci, and polypeptides, further references herein to D segments and elements will be in parentheses to indicate the inclusion of these regions only in the appropriate TCR chains. Thus, V(D)J refers either to VDJ sequences of chains which have a D region or refers to VJ sequences of chains lacking D regions.)

During lymphocyte maturation, single V, (D) and J gene segments are rearranged to form a functional gene that determines the amino acid sequence of the TCR expressed by that cell. Since the pool of V, (D) and J genes which may be rearranged is multi-membered and since individual members of these pools may be rearranged in virtually any combination, the complete TCR repertoire is highly diverse and capable of specifically recognizing and binding the vast array of binding partners to which an organism may be exposed. However, a particular T cell will have only one TCR molecule and that TCR molecule, to a large degree if not singly, determines the specificity of that T cell for its binding partner.

Animal models have contributed significantly to our understanding of the immunological mechanisms of autoimmune disease. One such animal model, experimental allergic encephalomyelitis (EAE), is an autoimmune disease of the central nervous system that can be induced in mice and rats by immunization with myelin basic protein (MBP). The disease is characterized clinically by paralysis and mild wasting and histologically by a perivascular mononuclear cell infiltration of the central nervous system parenchyma. The disease pathogenesis is mediated by T cells with specificity for MBP. Multiple clones of MBP-specific T cells have been isolated from animals suffering from EAE and have been propagated in continuous culture. After in vitro stimulation with MBP, these T cell clones rapidly induce EAE when adoptively transferred to healthy hosts. Importantly, these EAE-inducing T cells are specific, not only for the same antigen (MBP), but also usually for a single epitope on that antigen. These observations indicate that discrete populations of autoaggressive T cells are responsible for the pathogenesis of EAE.

Analysis of the TCRs of EAE-inducing T cells has revealed restricted heterogeneity in the structure of these disease-associated receptors. In one analysis of 33 MBP-reactive T cells, only two alpha chain V region gene segments and a single alpha chain J region gene segment were utilized. Similar restriction of beta chain TCR gene usage was also observed in this T cell population. Only two beta chain V region segments and two J region gene segments were found. More importantly, approximately eighty percent of the T cell clones had identical amino acid sequences across the region of beta chain V-D-J joining. These findings confirm the notion of common TCR structure among T cells with similar antigen specificities and indicate that the TCR is an effective target for immunotherapeutic strategies aimed at eliminating the pathogenesis of EAE.

Various attempts have been made to exploit the antigen specificity of autoaggressive T cells in devising treatment strategies for EAE. For example, passive administration of monoclonal antibodies specific for TCRs present on EAE-inducing T cells has been employed. In the mouse model of EAE, infusion of a monoclonal antibody specific for $V_\beta 8$, the major beta chain V region gene used by MBP-specific T cells, reduced the susceptibility of mice to subsequent EAE induction (Acha-Orbea et al., Cell 54:263–273 (1988) and Urban et al., Cell 54:577–592 (1988)). Similar protection has been demonstrated in rat EAE with monoclonal antibody reactive with an unidentified idiotypic determinant of the TCR on MBP specific T cells (Burns et al., J. Exp. Med. 169:27–39 (1989)). While passive antibody therapy appears to have some ameliorative effect on EAE susceptibility, it is fraught with potential problems. The protection afforded is transient, thus requiring repeated administration of the antibody. Multiple infusions of antibody increases the chances that the host will mount an immune response to the administered antibody, particularly if it is raised in a xenogeneic animal. Further an antibody response to a pathogenic T cell clone represents only one element in the complete immune response and neglects the potential contributions of cellular immunity in resolving the autoreactivity.

The role of cellular immunity in reducing the activity of autoaggressive T cells in EAE has been examined and potential therapies suggested. In a manner similar to the passive antibody approach, regulatory T cells have been derived ex vivo and readministered for immunotherapy. For example, Sun et al., Nature, 332:843–845 (1988), have recently isolated a CD8+ T cell line from convalescing rats in whom EAE had been induced by adoptive transfer of an MBP-specific CD4+ T cell line. This CD8+ T cell line displayed cytolytic activity in vitro for the CD4+ T cell used to induce disease. Moreover, adoptive transfer of this CTL line reduced the susceptibility of recipient rats to subsequent challenge with MBP. Lider et al., Science, 239:181–183 (1988) have also isolated CD8+ T cells with suppressive activity for EAE-inducing T cells. These CD8+ cells were isolated from rats vaccinated with attenuated disease-inducing T cell clones and, though they showed no cytolytic activity in vitro, they could suppress MBP-driven proliferation of EAE-inducing T cells. Although these studies indicate that the CD8+ T cells could downregulate EAE, it is hard to reconcile a major role for these selected CD8+ CTLs in the long-term resistance of the recovered rats since Sedgwick, et al., (Eur. J. Immunol., 18:495–502 (1988)) have clearly shown that depletion of CD8+ cells with monoclonal antibodies does not affect the disease process or recovery.

In the experiments of Sun et al., and Lider et al., described above, the administration of extant derived regulatory T cells overcomes the major obstacle of passive antibody therapy; it permits a regulatory response in vivo of prolonged duration. However, it requires in vitro cultivation with attenuated disease-inducing T cells to develop clones of such regulatory T cells, a costly and labor intensive process. Further, in an outbred population such as humans, MHC non-identity among individuals makes this a highly individualized therapeutic strategy. Regulatory clones need to be derived for each individual patient and then re-administered only to that patient to avoid potential graft versus host reactions.

Direct vaccination with attenuated disease-inducing T cell clones also has been employed as a therapy for EAE. MBP-specific T cells, capable of transferring disease, have been attenuated by gamma irradiation or chemical fixation and used to vaccinate naive rats. In some cases, vaccinated animals exhibited resistance to subsequent attempts at EAE induction (Lider et al., supra; see Cohen and Weiner, Immunol. Today 9:332–335 (1988) for review). The effectiveness of such vaccination, however, is inconsistent and the degree of protection is highly variable. T cells contain a multitude of different antigens which induce an immune response when the whole T cell is administered as a vaccine. This phenomenon has been demonstrated by Offner et al., (J. Neuroimmunol., 21:13–22 (1989)), who showed that immunization with whole T cells increased the delayed type hypersensitivity (DTH) response, as measured by ear swelling, to those T cells in an incremental manner as the number of vaccinations increased. However, positive DTH responses were found in both protected and non-protected animals. Rats responded similarly to both the vaccinating encephalitogenic T cells and control T cells. Conversely, vaccination with PPD-specific T cells from a PPD-specific T cell line induced DTH to the vaccinating cells as well as to an encephalitogenic clone even though no protection was observed. The similar response of vaccinated rats to both disease-inducing and control cells, as quantified by delayed-type hypersensitivity (a measure of cell-mediated immunity), indicates that numerous antigens on these T cells are inducing immune responses. Thus, vaccination with attenuated disease-inducing T cells suffers from a lack of specificity for the protective antigen on the surface of that T cell, as well as, variable induction of immunity to that antigen. As a candidate for the treatment of human diseases, vaccination with attenuated T cells is plagued by the same labor intensiveness and need for individualized therapies as noted above for infusion of CD8+ cells.

The present invention provides an effective method of immunotherapy for T cell mediated pathologies, including autoimmune diseases, which avoids many of the problems associated with the previously suggested methods of treatment. By vaccinating, rather than passively administering heterologous antibodies, the host's own immune system is mobilized to suppress the autoaggressive T cells. Thus, the suppression is persistent and may involve any and all immunological mechanisms in effecting that suppression. This multi-faceted response is more effective than the uni-dimensional suppression achieved by passive administration of monoclonal antibodies or extant-derived regulatory T cell clones.

As they relate to autoimmune disease, the vaccines of the present invention comprise TCRs of T cells that mediate autoimmune diseases. The vaccines can be whole TCRs substantially purified from T cell clones, individual T cell receptor chains (for example, alpha, beta, etc.) or portions of such chains, either alone or in combination. The vaccine can be homogenous, for example, a single peptide, or can be composed of more than one type of peptide, each of which corresponds to a different portion of the TCR. Further, these peptides can be from distinct TCRs wherein both TCRs contribute to the T cell mediated pathology.

In a specific embodiment, the immunizing peptide can have the amino acid sequence SGDQGGNE when the subject has multiple sclerosis. Any immunogenic portion of this peptide can be effective. Thus, amino acid substitutions can be made which do not destroy the immunogenicity of the peptide. Additionally, this peptide can be linked to a carrier to further increase its immunogenicity. Alternatively, whole T cell receptors which include this sequence can be used to vaccinate directly.

In a further specific embodiment, T cell receptors, whole T cells or fragments of the TCR which contain Vβ17 can be used to immunize an individual having a T cell mediated pathology to treat or prevent the disease. In a specific embodiment, rheumatoid arthritis can be so treated. The immune response generated in the individual can neutralize or kill T cells having Vβ17 and, thus, prevent or treat the deleterious effects of Vβ17-bearing T cells. Moreover, to the extent that Vβ17 is common to T cell receptors on pathogenic T cells mediating autoimmune diseases in general, such vaccines can also be effective in ameliorating such other autoimmune diseases.

By "substantially pure" it is meant that the TCR is substantially free of other biochemical moieties with which it is normally associated in nature. Alternatively, the vaccines comprise peptides of varying lengths corresponding to the TCR or portions thereof. The peptides can be produced synthetically or recombinantly, by means well known to those skilled in the art. Preferably, the peptide vaccines correspond to regions of the TCR which distinguish that TCR from other nonpathogenic TCRs. Such specific regions can be located within the various region(s) of the respective TCR polypeptide chains, especially a short sequence spanning the V(D)J junction, thus restricting the immune response solely to those T cells bearing this single determinant.

The vaccines are administered to a host exhibiting or at risk of exhibiting an autoimmune response. Definite clinical diagnosis of a particular autoimmune disease warrants the administration of the relevant disease-specific TCR vaccines. Prophylactic applications are warranted in diseases where the autoimmune mechanisms precede the onset of overt clinical disease (for example, Type I Diabetes). Thus, individuals with familial history of disease and predicted to be at risk by reliable prognostic indicators could be treated prophylactically to interdict autoimmune mechanisms prior to their onset.

TCR vaccines can be administered in many possible formulations, in pharmacologically acceptable mediums. In the case of a short peptide, the peptide can be conjugated to a carrier, such as KLH, in order to increase its immunogenicity. The vaccine can be administered in conjunction with an adjuvant, various of which are known to those skilled in the art. After initial immunization with the vaccine, a booster can be provided. The vaccines are administered by conventional methods, in dosages which are sufficient to elicit an immunological response, which can be easily determined by those skilled in the art.

Appropriate peptides to be used for immunization can be determined as follows. Disease-inducing T cell clones reactive with the target antigens are isolated from affected individuals. Such T cells are obtained preferably from the site of active autoaggressive activity such as a lesion in the case of pemphigus vulgaris, central nervous system (CNS) in the case of multiple sclerosis or synovial fluid or tissue in the case of rheumatoid arthritis, or alternatively from blood of affected individuals. The TCR genes from these autoaggressive T cells are then sequenced. Polypeptides corresponding to TCRs or portions thereof that are selectively represented among disease inducing T cells (relative to non-pathogenic T cells) can then be selected as vaccines and made and used as described above.

Alternatively, the vaccines can comprise anti-idiotypic antibodies which are internal images of the peptides described above. Methods of making, selecting and administering such anti-idiotype vaccines are well known in the art. See, for example, Eichmann, et al., CRC Critical Reviews in Immunology 7:193–227 (1987), which is incorporated herein by reference.

T Cell Pathologies of Malignant Etiology

To illustrate the utility of TCR vaccination, autoimmune disease has been discussed. However, T cell lymphoma is another T cell pathology which would be amenable to this type of treatment. Application of this technology in the treatment of T lymphoma would be conducted in virtually identical fashion. In one respect, however, this technology is more readily applied to T cell proliferative disease since the isolation of the pathogenic T cells is more easily accomplished. Once the clones are isolated, the technology is applied in the manner described herein. Specifically, the TCR genes of the T lymphomas are sequenced, appropriate regions of those TCRs are identified and used as vaccines. The vaccines can comprise single or multiple peptides, and can be administered in pharmacologically acceptable formulations with or without adjuvants by conventional means.

Multiple Sclerosis

T cells causative of multiple sclerosis (MS) have not previously been identified, though MBP-reactive T cells have been proposed to play a role due to the clinical and histologic similarities between MS and EAE. In rat and mouse models of EAE, MBP-reactive, encephalogenic T cells show striking conservation of β-chain VDJ amino acid sequence, despite known differences in MHC restriction and MBP-peptide antigen specificity. This invention is premised on the observation that a human myelin basic protein (MBP)-reactive T cell line, derived from an MS patient, has a TCR β-chain with a VDJ amino acid sequence homologous with that of β-chains from MBP-reactive T cells mediating pathogenesis in experimental allergic encephalomyelitis (EAE), an animal model of MS. This line is specific for another epitope of MBP. This finding demonstrates the involvement of MBP-reactive T cells in the pathogenesis of MS and demonstrates that TCR peptides similar to those described herein for the prevention of EAE can be appropriate in treating MS.

Rheumatoid Arthritis

Rheumatoid arthritis (RA) is a T cell mediated autoimmune disease. The invention describes clonal infiltrates of activated Vβ17 T cells in the synovium of rheumatoid arthritis patients. The presence of these T cells in the diseased tissue of all patients examined, their clonality, and the cytotoxic activity of one such T cell for synovial adherent cells, demonstrates a central role for Vβ17 bearing T cells in the pathogenesis of RA.

Activated T cell populations in the synovial tissue of RA patients have been examined by analyzing T cell receptor (TCR) mRNAs isolated from IL-2 receptor positive (IL-2R+) synovial T cells. TCR mRNAs were amplified using a polymerase chain reaction (PCR) protocol designed to amplify human TCR β-chain genes containing virtually any Vβ gene element. In this analysis, clonal Vβ17 rearrangements were found to be enriched in the IL2-R+ population, indicating that Vβ17 T cells are likely involved in the pathogenesis of RA. A CD4+, Vβ17 bearing T cell clone has been isolated from one of the synovial tissue specimens and its in vitro cytotoxicity for synovial adherent cells supports the direct involvement of Vβ17 T cells in RA.

As noted, the invention provides the extremely important discovery that a specific variable region of the β-chain of the TCR, designated Vβ17, is closely associated with T cell mediated pathologies, especially rheumatoid arthritis in human subjects. This discovery allows for the detection, prevention and treatment of rheumatoid arthritis using the methodology set out in this invention. Similar therapeutic approaches set out above for EAE can be applied to rheumatoid arthritis by those skilled in the art.

Specifically, the invention provides a method of diagnosing or predicting susceptibility to T cell mediated pathologies in an individual comprising detecting T cells having the β-chain variable region designated Vβ17 in a sample from the individual, the presence of abnormal levels of Vβ17-containing T cells indicating the pathology or susceptibility to the pathology. The Vβ17 containing T cell can be qualitatively or quantitatively compared to that of normal individuals. Such diagnosis can be performed for example by detecting a portion of the Vβ17 which does not occur on non-rheumatoid arthritis associated β-chain variable region T-cell receptors. The Vβ17 can be detected, for example, by contacting the Vβ17 with a detectable ligand capable of specifically binding to Vβ17. Many such detectable ligands are known in the art, e.g. an enzyme linked antibody. Alternatively, nucleotide probes complementary to Vβ17 encoding nucleic acid sequences can be utilized to detect Vβ17 containing T cells, as taught in Example IX.

The invention also provides a method of preventing or treating a T cell mediated pathology comprising preventing the attachment of a Vβ17 containing T-cell receptor to its binding partner. In one embodiment attachment is prevented by binding a ligand to Vβ17. In an alternative embodiment attachment is prevented by binding a ligand to the Vβ17 binding partner. Attachment can be prevented by known methods, e.g. binding an antibody to Vβ17 or the binding partner to physically block attachment.

The invention also provides a method of preventing or treating a T cell mediated pathology in an individual comprising cytotoxicly or cytostaticly treating Vβ17 containing T-cells in the individual. In one embodiment, the Vβ17 containing T-cells are treated with a cytotoxic or cytostatic agent which selectively binds Vβ17. The agent can be an antibody attached to a radioactive or chemotherapeutic moiety. Such attachment and effective agents are well known in the art. See, for example, Harlow, E. and Lane, *Antibodies, A Laboratory Manual*, Cold Spring Harbor Laboratory, 1988, which is incorporated herein by reference.

The invention also provides the extremely important discovery that a specific TCR sequence, SGDQGGNE, is closely associated with multiple sclerosis in human subjects. This discovery allows for the detection, prevention and treatment of multiple sclerosis using the methodology set out in this invention. Similar therapeutic approaches set out herein for EAE can be applied to multiple sclerosis by those skilled in the art.

Specifically, the invention provides a method of diagnosing or predicting susceptibility to multiple sclerosis in an individual comprising detecting T cells having substantially the SGDQGGNE sequence in a sample from the individual, the presence of the sequence indicating multiple sclerosis or susceptibility to multiple sclerosis. The sequence can be detected, for example, by contacting it with a detectable ligand. Many such ligands are known in the art, e.g. an enzyme linked antibody. Alternatively, nucleotide probes complementary to the nucleic acid encoding the sequence can be utilized to detect T cells as, taught in Example IX.

The invention also provides a method of preventing or treating multiple sclerosis comprising preventing the attachment of a T-cell receptor containing substantially the SGDQGGNE sequence to its binding partner. In one embodiment attachment is prevented by binding a ligand to the sequence. In an alternative embodiment attachment is prevented by binding a ligand to the binding partner. Attachment can be prevented by known methods, e.g. binding an antibody to the sequence to physically block attachment.

The invention also provides a method of preventing or treating multiple sclerosis in an individual comprising cytotoxicly or cytostaticly treating T cells containing substantially the SGDQGGNE sequence in the individual. In one embodiment, T-cells are treated with a cytotoxic or cytostatic agent which selectively binds the sequence. The agent can be an antibody attached to a radioactive or chemotherapeutic moiety.

The following examples are intended to illustrate but not limit the invention.

EXAMPLE I

Rat Model of EAE

Female Lewis rats, (Charles River Laboratories, Raleigh-Durham, N.C.) were immunized in each hind foot pad with 50 μg of guinea pig myelin basic protein emulsified in complete Freund's adjuvant. The first signs of disease were typically observed 9–11 days post-immunization. Disease severity is scored on a three point scale as follows: 1=limp tail; 2=hind leg weakness; 3=hind leg paralysis. Following a disease course of approximately four to six days, most rats spontaneously recovered and were refractory to subsequent EAE induction.

EXAMPLE II

Selection and Preparation of Vaccines

Vaccinations were conducted with a T cell receptor peptide whose sequence was deduced from the DNA sequence of a T cell receptor beta gene predominating among EAE-inducing T cells of B10. PL mice. The DNA sequence was that reported by Urban, et al., supra, which is incorporated herein by reference. A nine amino acid peptide, having the sequence of the VDJ junction of the TCR beta chain of the mouse, was synthesized by methods known to those skilled in the art. The sequence of this peptide is: SGDAGGGYE. (Amino acids are represented by the conventional single letter codes.) The equivalent sequence in the rat has been reported to be: SSD-SSNTE (Burns et al., J. Exp. Med. 169:27–39 (1989)). The peptide was desalted by Sephadex G-25 (Pharmacia Fine Chemicals, Piscataway, N.J.) column chromatography in 0.1 M acetic acid and the solvent was subsequently removed by two cycles of lyophilization. A portion of the peptide was conjugated to keyhole limpet hemocyanin (KLH) with glutaraldehyde at a ratio of 7.5 mgs of peptide per mg of KLH. The resulting conjugate was dialyzed against phosphate buffered saline (PBS).

EXAMPLE III

Vaccination Against EAE

Vaccines used in these studies consisted of free VDJ peptide and also of VDJ peptide conjugated to KLH. These were dissolved in PBS and were emulsified with equal volumes of either (1) incomplete Freund's adjuvant (IFA) or (2) complete Freund's adjuvant (CFA) made by suspending 10 mg/ml heat killed desiccated *Mycobacterium tuberculosis* H37ra (Difco Laboratories, Detroit, Mich.) in IFA. Emulsions were administered to 8–12 week old female Lewis rats in a final volume of 100 microliters per animal (50 μl in each of the hind footpads). 5 μg of unconjugated VDJ peptide were administered per rat. KLH-VDJ conjugate was administered at a dose equivalent to 10 μg of KLH per rat. Twenty-nine days later each rat was challenged with 50 μg of guinea pig myelin basic protein in complete Freund's adjuvant in the front footpads. Animals were monitored daily beginning at day 9 for clinical signs of EAE and were scored as described above. The results are presented in Table I. As can be seen, not only was there a reduced incidence of the disease in the vaccinated individuals, but in those which did contract the disease, the severity of the disease was reduced and/or the onset was delayed. The extent of protection varied with the vaccine formulation, those including CFA as the adjuvant demonstrating the greatest degree of protection.

TABLE I

| Animal No. | Vaccination (Adjuvant) | Days After Challenge ||||||||| 
|---|---|---|---|---|---|---|---|---|---|
| | | 10 | 11 | 12 | 13 | 14 | 15 | 16 | 17 | 18 |
| 1 | VDJ (IFA) | — | — | 2 | 3 | 3 | 3 | — | — | — |
| 2 | " | — | — | 1 | 3 | 3 | 3 | 2 | — | — |
| 3 | " | — | — | — | 3 | 3 | 3 | 2 | — | — |
| 4 | VDJ (CFA) | — | — | — | — | 1 | 1 | 1 | — | — |
| 5 | " | — | — | — | — | — | — | — | — | — |
| 6 | " | — | — | — | 1 | 3 | 3 | 3 | 2 | — |
| 7 | KLH-VDJ (CFA) | — | — | — | 1 | 3 | 2 | — | — | — |
| 8 | " | — | — | — | — | 1 | 1 | 1 | 1 | — |
| 9 | " | — | — | — | — | — | — | — | — | — |
| 10 | KLH-VDJ (IFA) | — | 1 | 3 | 3 | 2 | 2 | 1 | — | — |
| 11 | " | — | — | 3 | 3 | 3 | 3 | 3 | 2 | — |
| 12 | " | — | — | 1 | 3 | 3 | 3 | 3 | — | — |
| 13 | NONE | 1 | 3 | 3 | 3 | 3 | 1 | — | — | — |
| 14 | " | — | 1 | 3 | 3 | 3 | 1 | — | — | — |
| 15 | " | 1 | 3 | 3 | 3 | 1 | — | — | — | — |

Scoring:
— no signs

13

TABLE I-continued

| Animal No. | Vaccination (Adjuvant) | 10 | 11 | 12 | 13 | 14 | 15 | 16 | 17 | 18 |
|---|---|---|---|---|---|---|---|---|---|---|

1) limp tail
2) hind leg weakness
3) hind leg paralysis

EXAMPLE IV

Vaccination Against EAE With Lewis Rat VDJ Peptides

The VDJ peptide used in the previous examples was synthesized according to the sequence of TCR β chain molecules found on EAE-inducing T cells in B10.PL mice. In addition, peptides were synthesized and tested which correspond to sequences found on encephalitogenic T cells in Lewis rats. These VDJ sequences are homologous with that of B10.PL mice, but not identical. The rat peptides synthesized according to the DNA sequences reported by Burns, et al. and Chluba, et al., Eur. J. Immunol. 19:279–284 (1989). The sequences of these peptides designated IR1, 2, 3 and 9b are shown below, aligned with the B10.PL mouse sequence used in Examples I through III (VDJ).

```
VDJ        S G D A G G Y E
IR1    C A S S D — S S N T E V F F G K
IR2    C A S S D — S G N T E V F F G K
IR3    C A S S D — S G N — V L Y F G E G S R
IR9b     A S S D — S S N T E
```

The preparation, administration and evaluation of these vaccines were conducted as described in Examples I through III with the following exceptions: 50 μg of the individual VDJ peptides were incorporated into vaccine formulations containing CFA; neither vaccinations in IFA nor vaccinations with peptides conjugated to KLH were conducted. Control animals were untreated prior to MBP challenge as in Example III or were vaccinated with emulsions of PBS and CFA to assess the protective effect of adjuvant alone. The results are shown in Table II below.

TABLE II

| Animal No. | Vaccination (Adjuvant) | 10 | 11 | 12 | 13 | 14 | 15 | 16 | 17 | 18 |
|---|---|---|---|---|---|---|---|---|---|---|
| 1 | None | — | 1 | 2 | 3 | 3 | 2 | — | — | — |
| 2 | " | 1 | 3 | 3 | 3 | 2 | — | — | — | — |
| 3 | " | — | 2 | 3 | 3 | 3 | 1 | — | — | — |
| 4 | PBS-CFA | 1 | 2 | 3 | 3 | 3 | — | — | — | — |
| 5 | " | 1 | 2 | 3 | 3 | 3 | — | — | — | — |
| 6 | " | — | 2 | 3 | 3 | 3 | — | — | — | — |
| 7 | IR1 (50 μg) | — | — | — | 2 | 1 | — | — | — | — |
| 8 | " | — | — | — | — | 1 | 3 | — | — | — |
| 9 | " | — | — | — | 1 | 1 | 1 | 1 | — | — |
| 10 | IR2 (50 μg) | — | — | 1 | 3 | 3 | 3 | — | — | — |
| 11 | " | — | — | — | — | 2 | 2 | 3 | 3 | — |
| 12 | " | — | — | — | — | 1 | — | — | — | — |
| 13 | IR3 (50 μg) | 1 | 3 | 3 | 3 | 2 | — | — | — | — |
| 14 | " | — | — | 2 | 3 | 3 | — | — | — | — |
| 15 | " | — | — | — | — | — | — | — | — | — |
| 16 | IR9b (50 μg) | — | — | — | — | — | — | — | — | — |
| 17 | " | — | — | — | — | — | — | — | — | — |
| 18 | " | — | — | — | — | — | — | — | — | — |
| 19 | " | — | — | — | — | — | — | — | — | — |

Scoring:
— no signs
1) limp tail
2) hind leg weakness
3) hind leg paralysis

As shown in Table II, disease in unvaccinated control animals was observed as early as day 10. Disease was characterized by severe paralysis and wasting, persisted for 4 to 6 days and spontaneously remitted. PBS-CFA vaccinated rats displayed disease courses virtually indistinguishable from those of unvaccinated controls. In contrast, delays in onset were observed in some of the IR1, 2 or 3 vaccinated animals and others showed both delayed onset as well as decreased severity and/or duration of disease. Overall, however, vaccinations with the rat VDJ peptides (IR1–3) were slightly less effective than those with the mouse VDJ peptide (Example III). Vaccination with IR9b, however, afforded complete protection in all four animals in which it was tested. Importantly, no histologic lesions characteristic of disease were found in any of the four animals vaccinated with IR9b indicating that sub-clinical signs of disease were also abrogated.

EXAMPLE V

Vaccination With V Region Specific Peptides

A peptide specific for the Vβ8 gene family was tested as a vaccine against EAE. Vβ8 is the most common β chain gene family used by encephalitogenic T cells in both rats and mice. A peptide was synthesized based on a unique DNA sequence found in the Vβ8 gene, and which is not found among other rat Vβ genes whose sequences were reported by Morris, et al., Immunogenetics 27:174–179 (1988). The sequence of this Vβ8 peptide, designated IR7, is:

IR7 D M G H G L R L I H Y S Y D V N S T E K

The efficacy of this Vβ8 peptide was tested in the Lewis rat model of EAE (Example I) as described in Examples II and III. 50 μg of peptide were tested in CFA. Vaccinations in IFA or with peptide-KLH conjugates were not conducted. The results of these studies are shown in Table III.

TABLE III

| Animal No. | Vaccination (Adjuvant) | Days After Challenge | | | | | | | | |
|---|---|---|---|---|---|---|---|---|---|---|
| | | 10 | 11 | 12 | 13 | 14 | 15 | 16 | 17 | 18 |
| 1 | IR7 (50 µg) | — | — | 1 | 2 | 3 | 3 | 3 | — | — |
| 2 | " | — | — | — | — | 1 | 1 | — | — | — |
| 3 | " | — | — | — | — | — | — | — | — | — |

Scoring:
— no signs
1) limp tail
2) hind leg weakness
3) hind leg paralysis

The results of vaccinations conducted with the rat Vβ8 peptide are similar to those observed with the mouse and rat IR1, 2 and 3 peptides. Delayed onset as well as decreased severity and duration of disease was observed in one animal. One animal was completely protected.

EXAMPLE VI

Vaccination With J Region Peptides

A peptide was synthesized which corresponds to the J α gene segment, TA39, found among both rat and mouse encephalitogenic T cell receptors. The sequence of this peptide, designated IR5, is:

IR5 R F G A G T R L T V K

The efficacy of the JαTA39 peptide was tested in the Lewis rat model of EAE (Example I) as described in Examples II and III. 50 µg of peptide were tested in CFA. Vaccinations in IFA or with peptide-KLH conjugates were not conducted. The results of these studies are shown in Table IV.

TABLE IV

| Animal No. | Vaccination (Adjuvant) | Days After Challenge | | | | | | | | | | |
|---|---|---|---|---|---|---|---|---|---|---|---|---|
| | | 10 | 11 | 12 | 13 | 14 | 15 | 16 | 17 | 18 | 19 | 20 |
| 1 | IR5 (50 µg) | — | — | — | — | — | — | 2 | 1 | 1 | 1 | 1 | — |
| 2 | " | — | — | — | — | — | — | — | — | — | — | — |
| 3 | " | — | — | — | — | — | — | — | — | — | — | — |

Scoring:
— no signs
1) limp tail
2) hind leg weakness
3) hind leg paralysis

The results of vaccinations conducted with the rat J α TA39 peptide are more effective than those observed with the mouse VDJ peptide or the Vβ8 peptide. Two of three animals were totally protected and, in the third, disease onset was markedly delayed. Severity was also reduced in this animal though disease persisted for a normal course of 5 days. Importantly, the two animals which were completely protected showed no histologic evidence of T cell infiltration of the CNS. This result indicates that vaccinating with the JαTA39 very efficiently induces a regulatory response directed at encephalitogenic T cells. Even sub-clinical signs of disease were abrogated.

EXAMPLE VII

Vaccination With Mixtures of TCR Peptides

Vaccinations were conducted with a mixture of TCR peptides. This mixture contained 50 µg of each of the peptides IR1, 2, 3 and 5 (the three rat VDJ peptides and the rat JαTA39 peptide).

The efficacy of this peptide mixture was tested in the Lewis rat model (Example I) as described in Examples II and III. Peptides were tested in CFA. Vaccinations in IFA or with peptide-KLH conjugates were not conducted. The results of these studies are shown in Table V.

TABLE V

| Animal No. | Vaccination (Adjuvant) | Days After Challenge | | | | | | | | |
|---|---|---|---|---|---|---|---|---|---|---|
| | | 10 | 11 | 12 | 13 | 14 | 15 | 16 | 17 | 18 |
| 4 | IR1, 2, 3, 5 | — | — | — | — | — | — | — | — | — |
| 5 | (50 µg each) | — | — | — | — | — | — | — | — | — |
| 6 | " | — | — | — | — | — | — | — | — | — |

Scoring:
— no signs
1) limp tail
2) hind leg weakness
3) hind leg paralysis

The results of vaccinations conducted with the rat JαTA39 and three VDJ peptides were as effective as those described for IR9b in Table II. All three animals were totally protected. In addition to the absence of any clinical signs of EAE, two of these three animals were completely free of histological evidence of T cell infiltration into the CNS while the third showed only two small foci of lymphocytic infiltration at the base of the spinal cord.

EXAMPLE VIII

Multiple Sclerosis Vaccine

Human MBP-reactive T cells

MBP-reactive T cell lines were established from peripheral blood mononuclear cells (PBMC) of nine chronic progressive MS patients and two healthy controls. Cells were maintained in culture by regular stimulation with purified human MBP and irradiated-autologous PBMC for three days followed by four days in IL-2 containing medium.

PCR Amplification of TCR β-chain Genes From MBP-reactive T Cell Lines

T cells were harvested from log phase cultures and RNA was prepared, amplified with the Vβ16mer primer and nested Cβ primers for 55 cycles as described in Example IX.

TCR β-chain Sequences of Human MBP-reactive T Cells

Vβ16mer amplified TCR β-chain genes from human MBP-reactive T cell lines were sequenced using the Cβseq primer. Amplification products were gel purified, base denatured and sequenced from the Cβseq primer. Readable DNA sequence was obtained from 5 of these lines, indicating that predominant T cell clones had been selected by long term in vitro passage. One of these sequences, from the Re cell line (Table VI), possessed a β-chain VDJ amino acid sequence that shared five of the first six and six of nine total residues with the β-chain VDJ amino acid sequence conserved among MBP reactive, encephalogenic T cells in the B10.PL mouse model of EAE. This sequence was not present among the predominant TCR rearrangements found in the remaining four human MBP reactive T cell lines.

To determine if similar sequences were present in the β-chain repertoire of the MBP-reactive T cell lines from other MS patients, PCR amplification was conducted with a degenerate (n=1024) 21-nucleotide primer (VβRe) corresponding to seven amino acids of this sequence (Table VI). RNAs were reversed transcribed and amplified in 20 cycle stage I reactions with the Vβ16mer and Cβext primers. One μl aliquots of these stage I reactions were reamplified for 35 cycles with the VβRe and Cβ int primers. One μl aliquots of these reactions were analyzed by Southern blot hybridization with a $^{32}$P-labeled human Cβ probe. This analysis revealed the 300 bp amplified product in the Re cell line and in one of the other MS patient lines, but not in MBP-reactive T cells from control subjects or in non-MBP reactive human T cell lines and clones. The presence of this sequence in two of the nine MS patient lines tested is compelling. Since this sequence is known to be conserved among encephalogenic T cells in EAE, its detection among MBP-reactive T cells from MS patients demonstrates a role for T cells bearing this determinant in the pathogenesis of MS.

Immunogenic peptides having the sequence SGDQGGNE can be synthesized as shown in Example II and used to immunize human subjects by methods demonstrated in Example III. Such immunizations can result in an effective immune response.

FBS. This preselection with mouse IgG (mIgG) and magnetic beads was used to control for non-specific adsorption of T cells. The cells remaining in the initial suspension were further incubated 30 minutes at 0° C. with 5 μg/ml monoclonal mouse IgG reactive with the human T cell IL2-R (Coulter Immunology, Hialeah, Fla.). Cells were washed and selected with magnetic beads as above. Beads from the IgG preadsorption and the IL2-R antibody selection were immediately resuspended in acidified-guanidinium-phenol-chloroform and RNA prepared as described in Chonezynski and Sacchi, Anal. Biochem. 162:156 (1987), which is incorporated herein by reference. Since RNAS were prepared without in vitro culture of the cells and the accompanying bias that may be induced, they are expected to accurately reflect T cell distributions in synovial tissue at the time of surgical removal. Only half of the mIgG and αIL2-R beads from patient 1012 were immediately processed for RNA. The remainder were cultured for 5 days in RPMI 1640, 5% FBS, 20% HL-1 (Ventrex Laboratories Inc., Portland, Me.), 25 mM HEPES, glutamine, antibiotics and 20% LAK supernatant (Allegretta et al., Science, 247:718 (1990)), which is incorporated by reference herein, as a source of IL-2. RNA

TABLE VI

A) 
| Sample | Vb | Db | Jb |
|---|---|---|---|
| MS-Re | Vβ4.2<br>ctctgc<br>S G D | agcggagaccagggcggc<br>Q G G - | Jβ2.1<br>aatgagcagttcttc<br>N E Q F F |
| B10.PL | | S G D A G G G Y E | |

B)
```
              A         A  A
         C    C    A    C  C    C    A
    5' G G  G A  C A  G G  G G  A A  G A 3'
         G    T    G    G  G    T    G
         T         T    T
```

EXAMPLE IX

Detection of Clonal Infiltrates of Activated Vβ17 T Cells in the Synovium of Rheumatoid Arthritis Patients T Cell Preparations From Synovial tissue Synovial tissue specimens were obtained from radiographically proven rheumatoid arthritis patients undergoing joint replacement therapy. Activated T cells were selected using magnetic beads and antibodies reactive with the human IL2-R (αIL2-R) as follows. Synovial tissue was digested for 4 hrs at 37° C. in RPMI+10% Fetal Bovine Serum (FBS) containing 4 mg/ml collagenase (Worthington Biochemical, Freehold, N.J.) and 0.15 mg/ml DNAse (Sigma, St. Louis, Mo.). Digests were passed through an 80-mesh screen and single cells were collected by Ficoll density gradient centrifugation. Cells at the interface were washed and were incubated at 10$^6$/ml for 30 min at 0° C. with 5 μg/ml control mouse IgG (Coulter Immunology, Hialeah, Fla.) in PBS containing 2% FBS (PBS-FBS). Cells were washed three times and incubated for 30 min at 0° C. with magnetic beads conjugated to goat anti-mouse IgG (Advanced Magnetics, Cambridge, Mass.). Beads were magnetically separated and washed three times with PBSwas extracted from cultures of the αIL2-R beads (1012IL2.d5), but not from the 1012mIgG sample as no viable cells were present at the end of the 5 day culture.

A T cell clone was derived from the Ficoll pellet of patient 1008. The cells in the pellet were cultured at 2×10$^6$/ml in media without IL-2 for two weeks. Non-adherent cells from this culture were cloned by limiting dilution onto autologous synovial cell monolayers. A CD4+ T cell clone 1008.8 was obtained and adapted to culture by regular stimulation with autologous synovial monolayers for 3 days in media without IL-2 followed by a 4 day culture in medium with LAK supernatant.

Lysis of Synovial Adherent Cells by 1008.8

Lysis of synovial adherent cells by 1008.8 was demonstrated as follows. Synovial cell monolayers were labeled as described in Stedman and Campbell, J. Immunol. Meth. 119:291 (1989), which is incorporated herein by reference, with $^{35}$S for use as targets in CTL assays. Cells were typsinized, washed and plated at 2000 cells per well of a 96-well round bottom microtiter plate. 1008.8 cells, cultured for 3 days prior to the assay with synovial adherent cells and medium containing LAK supernatant, were added to the targets at the indicated effector:target ratios. Cultures were incubated overnight at 37° C., centrifuged at 300×g for 2 minutes and radioactivity in 50 μl of the supernatant quantified. Per cent specific lysis was calculated relative to detergent-lysed targets by standard formulas. This clone is cytotoxic for synovial adherent cell targets in CTL assays (Table VII).

TABLE VII

| Effector:Target Ratio | % Specific Lysis |
|---|---|
| 5:1 | 7 |
| 10:1 | 16 |
| 25:1 | 32 |

PCR Amplification of TCR β-chain Genes

Figure 1B:
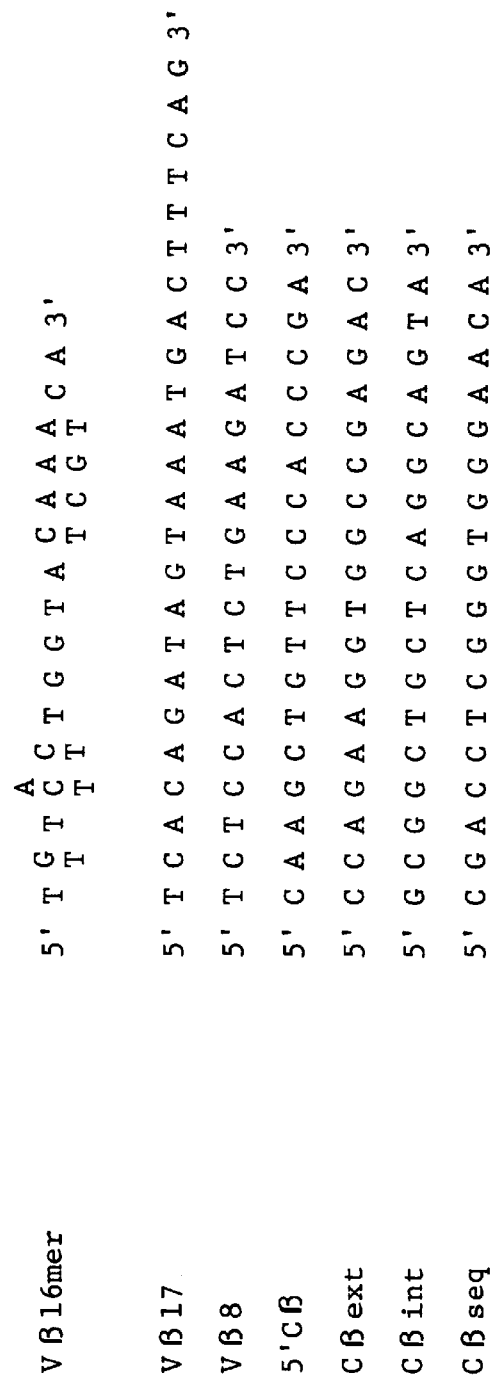

TCR β-chain genes were amplified with several combinations of the primers shown in FIG. 1. The Vβ16mer primer is a degenerate Vβ primer (n=256) which is predicted to bind 85% of human TCR β-chain genes at all 16 residues and 95% at 15 residues. This primer has been used to amplify TCR β-chains from more than 25 different human T cell clones, lines or primary tissue preparations. A spectrum of Vβ genes has been sequenced from these amplified DNAs, arguing against a significant bias of the primer for certain Vβ families. Thus, PCR amplification with the Vβ16mer primer facilitates analysis of T cell populations for which a priori knowledge of Vβ gene usage is unavailable.

T cell receptor β-chain genes were amplified in two-stage amplification reactions with nested pairs of the primers shown in FIG. 1. RNAs were reverse transcribed for 1 hour at 42° C. with 40 pmol of the Cβext primer in a 12 μl reaction using conditions described by Hart et al., The Lancet, p. 596 (1988), included by reference herein. Reactions were diluted with a master mix containing 40 pmols of the Vβ16mer primer, nucleotides and reaction buffer as above but without MgCl$_2$ to give a final Mg$^{+2}$ concentration of 3.6 mM. Samples were denatured for 15 minutes at 95° C., 1 unit of heat stable recombinant DNA polymerase (Cetus Corporation, Emeryville, Calif., Amplitaq™) was added and 20 cycles of PCR conducted. Each cycle consisted of a 1 min denaturation at 95° C., a two minute annealing step and a two minute extension at 72° C. The first two cycles were annealed at 37° C. and 45° C., respectively, and the remainder at 50° C. One microliter aliquots of these stage I reactions were added to 100 μl stage II amplification reactions (Cetus, Gene-Amp Kit™) containing 100 pmols of the Cβint primer and 100 pmols of the Vβ8, Vβ17 or 5'Cβ primers or 700 pmols of the Vβ16mer primer. Stage II amplifications were conducted as above with a 50° C. annealing temperature and without the 37° C. and 45° C. ramping.

RNA samples from 1012IL2.d5 and 1008.8 cultures were amplified with the Vβ16mer and Cβext primers in stage I reactions and with the Vβ16mer and the Cβint primer in 35 cycle stage II reactions. Reaction products, purified from low melting agarose gel slices with Gene Clean glass beads (Bio 1D1, San Diego, Calif.), were base denatured and sequenced from the Cβseq primer with T7 polymerase (Sequenase, United States Biochem, Cleveland, Ohio). A predominate Vβ sequence, corresponding to a single Vβ17 rearrangement Table VIII, was clearly readable in the 1012IL2.d5 sample. Other, less frequent rearrangements were detected as faint, uninterpretable background bands in the sequencing gels. Culture of these 1012.IL2 beads in IL2-containing medium without added accessory cells or antigen is not expected to induce de novo activation of T cells. Thus, the predominance of a single Vβ17 rearrangement in this sample reflects in vivo clonal expansion of Vβ17+ T cells in this patient. DNA sequence determination of TCR β-chain DNA amplified from the cytotoxic T cell clone, 1008.8, also revealed a Vβ17 rearrangement (Table VIII). The presence of Vβ17 rearrangements in these two different types of synovial T cell samples, derived from two separate RA patients, implicates Vβ17 bearing T cells in the pathogenesis of RA.

TABLE VIII

| Sample | Vb | Db | Jb |
|---|---|---|---|
| 1012 day 5 | Y L C A S<br>tatctctgtgccagt<br>Vβ17 | K N P T V S<br>aaaaatcccacggtctcc | Y G Y T F<br>tatggctacaccttc<br>Jβ1.2 |
| 1008.8 | Y L C A S<br>tatctctgtgccagt<br>Vβ17 | D N E S<br>gacaacgagagt | F F G Q G<br>ttctttggacaaggc<br>Jβ1.1 |
| 1014 IL-2 | Y L C A S<br>tatctctgtgccagt<br>Vβ17 | V R D R R<br>gtgagggacaggaga | N Y G Y T<br>aactatggctacacc<br>Jβ1.2 |
| 1015 IL-2 | Y L C A S S<br>tatctctgtgccagtagt<br>Vβ17 | S I D S<br>agtatagactcc | S Y E Q Y<br>tcctacgagcagtac<br>Jβ2.7 |

To determine whether or not Vβ17 rearrangements were present in the other magnetic bead RNA preparations, TCR β-chain genes were amplified with a Vβ17-specific primer in the second stage amplification after an initial amplification with the Vβ16mer (FIG. 1). Vβ17 TCR DNA could be amplified from magnetic bead samples derived from the 4 patients examined. Ethidium bromide staining of electrophoresed reaction products revealed greater Vβ17 amplification in some of the IL-2R+ samples than in the corresponding controls. Accordingly, the relative amounts of Vβ17 TCRs in each control and IL-2R+ sample were quantified by slot blot hybridization analysis as follows.

RNAs from magnetic bead preps were amplified in the first stage with the Vβ16mer and Cβext primers and then reamplified for twenty cycles with the Cβint primer and each of the Vβ17, Bβ8 and 5'Cβprimers. Amplification reactions were serially diluted in 20× SSC, denatured by boiling and chilled in an ice slurry. Samples were loaded onto nitrocellulose membranes, hybridized to a human TCR β-chain constant region probe and washed with 0.1× SSC, 0.1% SDS at 56° C. Bound radioactivity was quantified by liquid scintillation spectroscopy and endpoint dilutions were those samples with fewer than 200 cpm bound. The amounts of product produced by forty total cycles with each of the respective primer combinations falls in the linear portion of a product versus cycle number quantification curve.

Amplifications with the 5'Cβ and Cβint primer pair were used to estimate the total β-chain amplified from each sample, providing benchmarks for normalizing the results of Vβ17 and Vβ8 quantification in the respective IL-2R+ and control sample pairs (Table IX). The quantity of Vβ17 DNA amplified was increased in the IL-2R+ samples, relative to the control samples, in 3 of the 4 patients. The magnitude of the increase ranged from 5-fold in patient 1015 to 40-fold in patient 1014 (Table IX). This enrichment was not a product of the isolation procedure, since the quantity of Vβ8 DNA amplified was increased in the IL-2R+ fraction only in patient 1015.

TABLE IX

| | | | Endpoint Dilution | | | | |
|---|---|---|---|---|---|---|---|
| Sample | Cβ | Vβ17 | Vβ8 | Vβ17/Cβ | Vβ17IL-2R mIgG | Vβ8/Cβ | Vβ8IL-2 mIgG |
| 1 | 3,125 | 3,125 | 625 | 1 | 25 | 0.2 | 1 |
| 2 | 3,125 | 125 | 625 | 0.04 | | 0.2 | |
| 3 | 15,625 | 25 | 625 | 0.001 | 0.12 | 0.04 | 0.04 |
| 4 | 3,125 | 25 | 3,125 | 0.008 | | 1 | |
| 5 | 15,625 | 625 | 125 | 0.04 | 40 | 0.008 | 0.04 |
| 6 | 3,125 | 5 | 625 | 0.001 | | 0.2 | |
| 7 | 15,625 | 625 | 15,625 | 0.04 | 5 | 1 | 25 |
| 8 | 78,125 | 625 | 3,125 | 0.008 | | 0.04 | |

Sample 1 = 1012 IL-2R+,
Sample 2 = 1012 mIgG,
Sample 3 = 1013 IL-2R+,
Sample 4 = 1013 mIgG,
Sample 5 = 1014 IL-2R+,
Sample 6 = 1014 mIgG,
Sample 7 = 1015 IL-2R+,
Sample 8 = 1015 mIgG.

Vβ17 rearrangements from the IL-2R+ RNAs of the three patients showing enrichment were amplified with the Vβ17 and Cβint primer pair and the reaction products sequenced with the Cβseq primer. As was shown for sample 1012 IL-2.d5, 1014 and 1015 contained single sequences (Table XIII), indicative of clonal expansion of Vβ17 T cells in vivo. In contrast, direct sequencing of the rearrangements amplified with the Vβ8 specific primer was not possible due to significant heterogeneity in the β-chain product.

Vβ17 has the amino acid sequence MSNQVLCCVVL-CFLGANTVDG GITQSPKYLFRKEGQN-VTLSCEQNLNHDAMYWYRQDPGQGLR-LIYYSQIVNDFQKGD IAEGYSVSREKKESFPLTVTSAQKNPTAFYLCASS.

HLA-DR Analysis in Rheumatoid Arthritis Patients

Figure 2:
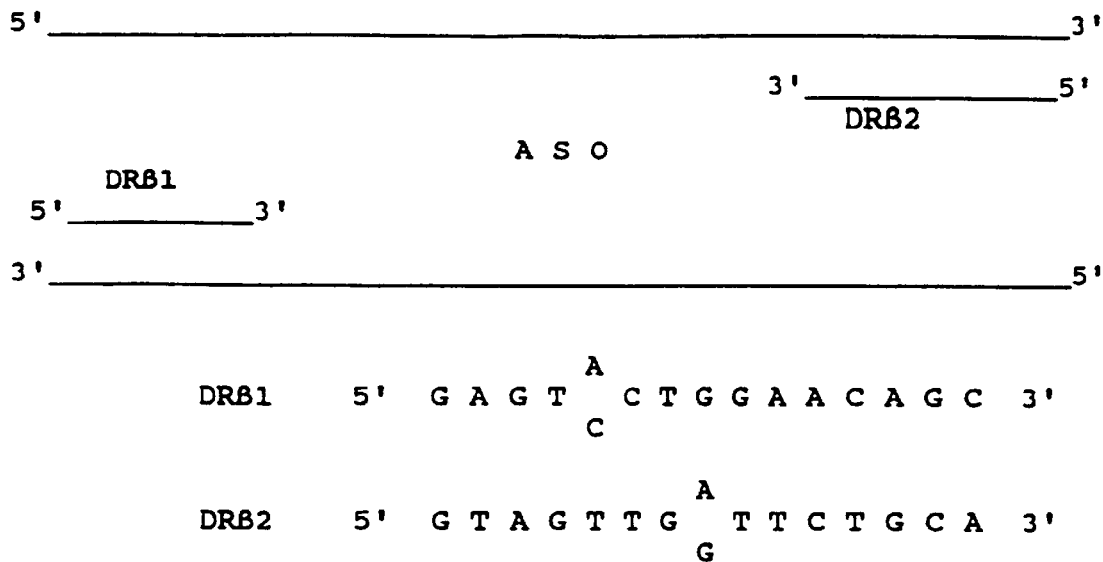
FIG. 2 shows the location and sequence of primers used in polymerase chain reaction amplification of HLA-DR $B_1$ genes. Also shown are HLA-DR allele specific oligonucleotides.

HLA-DR analysis in rheumatoid arthritis patients was performed as follows. DNA from each patient was prepared by boiling $10^5$ synovial cells in 200 μl dH$_2$O. Ten μl were amplified for 35 cycles in a 100 μl reaction (Cetus, Gene Amp Kit™) containing 100 pmols of each of the DRβ PCR primers (FIG. 2). One-tenth μl of this reaction was reamplified in 10 μls containing only the DRβ2 primer and 17 pmol of α32P-dCTP as the sole source of dCTP for 10 cycles. Reactions were spiked with 200 uM dCTP and chased for 2 cycles. The resulting negative strand probes were hybridized to slot blots containing 10 pmol of the HLA-DR allele specific oligos (positive strands) using conditions previously described by Amar et al., J. Immunol. 138:1947 (1987), which is incorporated herein by reference. The slots were washed twice for 20 minutes with tetramethylammoniumchloride (Wood et al., Proc. Natl. Acad. Sci. U.S.A. 82:1585 (1985)) which is incorporated herein by reference) at 65–68° C. and exposed to X-ray film.

Each of the patients in this study possessed at least one allele of the HLA-DR genes, DR4w4, DR1, DR4w14 or DR4w15, that are known to predispose for RA (FIG. 2).

T cell receptors containing Vβ17 or fragments thereof which are immunogenic or can be made immunogenic can be used to immunize human subjects by methods demonstrated by Example VII. Such immunizations can result in an effective immune response.

Although the invention has been described with reference to the presently-preferred embodiment, it should be understood that various modifications can be made without departing from the spirit of the invention. Accordingly, the invention is limited only by the following claims.

We claim:

1. A method of treating rheumatoid arthritis in a human individual comprising binding Vβ17 containing T cells in the individual with an effective amount of a cytotoxic or cytostatic agent specifically reactive with Vβ17 to kill or inhibit proliferation of said T cells, wherein said agent is an antibody.

2. The method of claim 1, wherein said antibody is attached to a moiety selected from the group consisting of radioactive moieties, chemotherapeutic moieties and chemotoxic moieties.

* * * * *